United States Patent [19]
Fleisch et al.

[11] Patent Number: 5,817,684
[45] Date of Patent: Oct. 6, 1998

[54] LEUKOTRIENE ANTAGONISTS FOR USE IN THE TREATMENT OR INHIBITION OF CEREBRAL FOCAL STROKE

[75] Inventors: Jerome H. Fleisch, Carmel; William T. Jackson; Jason S. Sawyer, both of Indianapolis, all of Ind.

[73] Assignee: Eli Lilly and Company, Indianapolis, Ind.

[21] Appl. No.: 982,600

[22] Filed: Dec. 2, 1997

Related U.S. Application Data

[60] Provisional application No. 60/033,180 Dec. 13, 1996 and provisional application No. 60/040,872 Mar. 21, 1997.

[51] Int. Cl.⁶ ............................ A61K 31/19; A61K 31/41
[52] U.S. Cl. .................. 514/381; 514/232.8; 514/233.5; 514/237.7; 514/238.8; 514/239.2; 514/239.5; 514/252; 514/318; 514/332; 514/340; 514/343; 514/346; 514/347; 514/351; 514/520; 514/521; 514/568; 514/570

[58] Field of Search ....................... 514/381, 568

[56] References Cited

U.S. PATENT DOCUMENTS 5,462,954  10/1995  Baker et al. ............................. 514/381

*Primary Examiner*—Leonard Schenkman
*Attorney, Agent, or Firm*—Arleen Palmberg; David E. Boone

[57] ABSTRACT

This invention provides methods for the treatment or prevention of cerebral focal ischemia which comprises administering to a mammal in need thereof an effective amount of a compound having activity as a leukotriene $B_4$ antagonist.

14 Claims, No Drawings

LEUKOTRIENE ANTAGONISTS FOR USE IN THE TREATMENT OR INHIBITION OF CEREBRAL FOCAL STROKE

This application claims the benefit of U.S. Provisional application Ser. Nos. 60/033,180, filed Dec. 13, 1996 and 60/040,872 filed Mar. 21, 1997

BACKGROUND OF THE INVENTION

Stroke remains the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by autoregulation. This phenomenon involves dilatation of downstream resistant vessels. Below the lower level of autoregulation (about 60 mm Hg), vasodilatation is inadequate and the cerebral blood flow falls. The brain, however, has perfusion reserves that can compensate for the fall in cerebral blood flow. This reserve exists because under normal conditions only about 35% of the oxygen delivered by the blood is extracted. Therefore, increased oxygen extraction can take place, provided that normoxia and normocapnea exist. When distal blood pressure falls below approximately 30 mm Hg, the two compensatory mechanisms (autoregulation and perfusion reserve) are inadequate to prevent failure of oxygen delivery.

As flows drops below the ischemic threshold of 23 ml/100 g/minute, symptoms of tissue hypoxia develop. Severe ischemia may be lethal. When the ischemia is moderate, it will result in "penumbra." In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. In other words, the penumbra is the tissue area that can be saved, and is essentially in a state between life and death.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagittal frontal lobe. Language disturbances manifested as decreased spontaneous speech may accompany generalized depression of psychomotor activity.

Most ischemic strokes involve portions or all of the territory of the middle cerebral artery with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contralateral loss of vision. Difficulty in reading (dyslexia) and in performing calculations (dyscalculia) may follow ischemia of the dominant posterior cerebral artery. Proximal occlusion of the posterior cerebral artery causes ischemia of the branches penetrating to calamic and limbic structures. The clinical results are hemisensory disturbances that may chronically change to intractable pain of the defective side (thalamic pain).

A significant event in cerebral ischemia is known as the transient ischemic attack ("TIA"). A TIA is defined as a neurologic deficit with a duration of less than 24 hours. The TIA is an important sign of an ischemic development that may lead to cerebral infarction. Presently, no ideal treatment for TIA exists, and there are no generally accepted guidelines as to whether medical or surgical procedures should be carried out in order to reduce the incidence of stroke in subjects with TIA.

The etiology of TIA involves hemodynamic events and thromboembolic mechanisms. Because most TIAs resolve within one hour, a deficit that lasts longer is often classified as presumptive stroke and is, accordingly, associated with permanent brain injury. Therefore, computed tomographic brain scans are used to search for cerebral infarction in areas affected by TIAs lasting longer than several hours. The relevant clinical distinction between a TIA and a stroke is whether the ischemia has caused brain damage, which is typically classified as infarction or ischemic necrosis. Subjects with deteriorating clinical signs might have stroke in evolution or are classified as having progressive stroke. In this clinical setting, clot propagation is possibly an important factor in disease progression.

There are a myriad of other diseases caused by or associated with ischemia. Vertebrobasilar ischemia is the result of the occlusion of the vertebral artery. Occlusion of the vertebral artery and interference with flow through the ipsilateral posterior inferior cerebellar artery causes lateral medullary syndrome, which has a symptomology including vertigo, nausea, vomiting nystagmus, ipsilateral ataxia and ipsilateral Herner's syndrome. Vertebrobasilar ischemia often produces multifocal lesions scattered on both sides of the brain stem along a considerable length. Except for cerebellar infarction and the lateral medullary syndrome, the clinical syndromes of discrete lesions are thus seldom seen in pure form. Vertebrobasilar ischemia manifests with various combinations of symptoms such as dizziness, usually vertigo, diplopia, facial weakness, ataxia and long tract signs.

A basilar artery occlusion produces massive deficits. One of these deficits is known as the "locked in state." In this condition, paralysis of the limbs and most of the bulbar muscle leaves the subject only able to communicate by moving the eyes or eyelids in a type of code. Occlusion of the basilar apex or top of the basilar is usually caused by emboli that lodge at the junction between the basilar artery and the two posterior cerebral arteries. The condition produces an initial reduction in arousal followed by blindness and amnesia due to an interruption of flow into the posterior cerebral arteries as well as abnormalities of vertical gaze and pupillary reactivity due to tegmental damage.

Venous occlusion can cause massive damage and death. This disease is less common than arterial cerebral vascular disease. As with ischemic stroke from arterial disease, the primary mechanism of brain damage is the reduction in capillary blood flow, in this instance because of increased outflow resistance from the blocked veins. Back transmission of high pressure into the capillary bed usually results in early brain swelling from edema and hemorrhagic infarction in subcortical white matter. The most dangerous form of venous disease arises when the superior sagittal sinus is occluded. Venous occlusion occurs in association with coagulation disorders, often in the purpural period, or in subjects with disseminated cancers or contagious diseases. If anticoagulant therapy is not initiated, superior sagittal sinus occlusion has a mortality rate of 25–40%.

Brief diffuse cerebral ischemia can cause syncope without any permanent sequelae. Prolonged diffuse ischemia in other organs have devastating consequences. The most common cause is a cardiac asystole or other cardiopulmonary failures, including infarction. Aortic dissection and global hypoxia or carbon monoxide poisoning can cause similar pictures. Diffuse hypoxia/ischemia typically kills neurons in the hippocampus, cerebellar Purkinje cells, striatum or cortical layers. Clinically, such a diffuse hypoxia/ischemia results in unconsciousness and in coma, followed in many instances by a chronic vegetative state. If the subject does not regain consciousness within a few days, the prognosis for the return of independent brain functions becomes very poor.

Other less common causes of cerebral focal stroke are hematologic diseases associated with thromboses. Such disorders include deficiencies of antithrombin III, protein C, or protein S; polycythemia vera; sickle cell anemia; disseminated intravascular coagulation; and thrombotic thrombocytopenic purpura (TTP). Exogenous agents such as oral contraceptives and ε-aminocaproic acid (EACA), drugs such as amphetamines and cocaine, and metabolic disorders, such as homocystinuria, have also been associated with cerebral thrombosis.

The eventual extent of neurologic recovery depends on the patient's age and general state of health as well as on the site and size of the infarction. Impaired consciousness, mental deterioration, aphasia, or severe brainstem signs all suggest a poor prognosis. Complete recovery is uncommon, but the sooner improvement begins, the better the prognosis. About 50% of patients with moderate or severe hemiplegia, and most of those with lesser deficits, recover functionally by the time of discharge and are ultimately able to care for their basic needs, have a clear sensorium, and can walk adequately, although use of an affected limb may be limited. Any deficit remaining after 6 months is likely to be permanent, although some patients continue to improve slowly. Recurrence of cerebral infarction is relatively common, and each recurrence is likely to add to the neurologic disability.

Research in the area of allergic reactions of the lung has provided evidence that arachidonic acid derivatives formed by the action of lipoxygenases are related to various disease states. Some of these arachidonic acid metabolites have been classified as members of a family eicosatetraenoic acids termed leukotrienes. Three of these substances are currently thought to be major components of what has been previously called slow reacting substance of anaphylaxis (SRS-A) and have been designated leukotrienes $C_4$, $D_4$, and $E_4$ ($LTC_4$, $LTD_4$, and $LTE_4$, respectively).

Another arachidonic acid metabolite, leukotriene $B_4$ ($LTB_4$), is a proinflammatory lipid which has been implicated in the pathogenesis of psoriasis, arthritis, chronic lung diseases, acute respiratory distress syndrome, asthma, inflammatory bowel diseases, and other inflammatory states characterized by the infiltration and activation of polymorphonuclear leukocytes and other proinflammatory cells. Thus activated, the polymorphonuclear leukocytes liberate tissue-degrading enzymes and reactive chemicals causing the inflammation. Antagonism of $LTB_4$ should therefore provide a novel therapeutic approach to treatment of these and other conditions. Activated microglial cells are the central nervous system analogues of systemic proinflammatory cells.

Because of the debilitating effects of cerebral focal stroke, there continues to exist a need for effective treatments.

SUMMARY OF THE INVENTION

This invention provides a method for the treatment or inhibiting of cerebral focal stroke in mammals comprising administering to a mammal in need thereof an effective amount of a compound Formula I

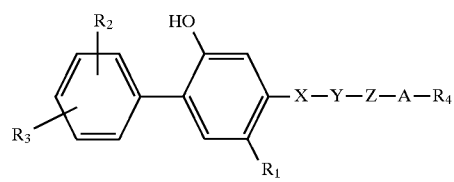

wherein:
$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substituted phenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)—S(O)q—, trifluoromethyl, or di-($C_1$–$C_3$ alkyl) amino;

X is —O—, —S—, —C(=O), or —CH$_2$—;

Y is —O— or —CH$_2$—;

or when taken together, —X—Y— is —CH=CH— or —C≡C—;

Z is a straight or branched chain $C_1$–$C_{10}$ alkylidenyl;

A is a bond, —O—, —S—, —CH=CH—, or —CR$_a$R$_b$—, where R$_a$ and R$_b$ are each independently hydrogen, $C_1$–$C_5$ alkyl, or R$_7$-substituted phenyl, or when taken together with the carbon atom to which they are attached form a $C_4$–$C_8$ cycloalkyl ring;

where,
- each $R_6$ is independently —COOH, 5-tetrazolyl, —CON$(R_9)_2$, or —CONHSO$_2R_{10}$;
- each $R_7$ is hydrogen, $C_1$–$C_4$ alkyl, $C_2$–$C_5$ alkenyl, $C_2$–$C_5$ alkynyl, benzyl, methoxy, -W-$R_6$, -T-G-$R_6$, ($C_1$–$C_4$ alkyl)-T-($C_1$–$C_4$ alkylidenyl)—O—, or hydroxy;
- $R_8$ is hydrogen or halo;
- each $R_9$ is independently hydrogen, phenyl, or $C_1$–$C_4$ alkyl, or when taken together with the nitrogen atom form a morpholino, piperidino, piperazino, or pyrrolidino group;
- $R_{10}$ is $C_1$–$C_4$ alkyl or phenyl;
- $R_{11}$ is $R_2$, -W-$R_6$, or -T-G-$R_6$;
- each W is a bond or straight or branched chain divalent hydrocarbyl radical of one to eight carbon atoms;
- each G is a straight or branched chain divalent hydrocarbyl radical of one to eight carbon atoms;
- each T is a bond, —CH$_2$—, —O—, —NH—, —NHCO—, —C(=O)—, or —S(O)q—;
- K is —C(=O)— or —CH(OH)—;
- each q is independently 0, 1, or 2;
- p is 0 or 1; and
- t is 0 or 1;
- provided when X is —O— or —S—, Y is not —O—;
- provided when A is —O— or —S—, $R_4$ is not $R_6$;
- provided when A is —O— or —S— and Z is a bond, Y is not —O—; and
- provided W is not a bond when p is 0;

or a pharmaceutically acceptable salt or solvate thereof.

DETAILED DESCRIPTION

The following definitions refer to the various terms used throughout this disclosure.

The term "$C_1$–$C_5$ alkyl" refers to the straight and branched aliphatic radicals of 1 to 5 carbon atoms such as methyl, ethyl, propyl, isopropyl, n-butyl, sec-butyl, tert-butyl, n-pentyl, 2,2-dimethylpropyl, hexyl, and the like. Included within this definition are the terms "$C_1$–$C_3$ alkyl" and "$C_1$–$C_4$ alkyl".

The term "$C_2$–$C_5$ alkenyl" refers to straight and branched aliphatic radicals of 2 to 5 carbon atoms containing one double bond, such as —CH=CH$_2$, —CH$_2$CH=CH$_2$, —CH$_2$CH$_2$CH=CH$_2$, —CH$_2$C(CH$_3$)=CH$_2$, —CH$_2$CH=C(CH$_3$)$_2$, and the like.

The term "$C_2$–$C_5$ alkynyl" refers to straight and branched aliphatic residues of 2 to 5 carbon atoms containing one triple bond, such as —C≡CH, —CH$_2$—C≡—CH, —CH$_2$CH$_2$C≡—CH, —CH$_2$CH(CH$_3$)C≡CH, —CH$_2$C≡CCH$_3$, and the like.

The term "$C_1$–$C_4$ alkoxy" refers to methoxy, ethoxy, propoxy, isopropoxy, butoxy, sec-butoxy, and tert-butoxy.

The term "halo" refers to fluoro, chloro, bromo, and iodo.

The term "$C_1$–$C_{10}$ alkylidenyl" refers to a divalent radical derived from a $C_1$–$C_{10}$ alkane such as —CH$_2$—, —CH(CH$_3$)—, —C(CH$_3$)$_2$—, —CH(C$_2$H$_5$)—, —CH$_2$CH$_2$—, —CH$_2$CH(CH$_3$)—, —CH(CH$_3$)CH$_2$—, —CH(CH$_3$)CH(CH$_3$)—, —CH$_2$C(CH$_3$)$_2$—, —CH$_2$CH(C$_2$H$_5$)—, —CH$_2$CH$_2$CH$_2$—, —CH(CH$_3$)CH$_2$CH$_2$—, —CH$_2$CH(CH$_3$)CH$_2$—, —CH$_2$CH(C$_2$H$_5$)CH$_2$—, —CH$_2$CH$_2$CH(C$_2$H$_5$)—, —C(CH$_3$)$_2$CH$_2$CH$_2$—, —CH(CH$_3$)CH$_2$CH(CH$_3$)—, —CH$_2$CH$_2$CH$_2$CH$_2$—, —CH$_2$C(CH$_3$)$_2$CH$_2$CH$_2$—, —CH$_2$C(CH$_3$)$_2$CH$_2$—, —CH$_2$CH$_2$CH(C$_2$H$_5$)CH$_2$—, —CH$_2$CH$_2$CH$_2$CH$_2$CH$_2$—, —CH(CH$_3$)CH$_2$CH$_2$CH$_2$CH$_2$—, —CH$_2$CH$_2$CH$_2$CH$_2$CH$_2$CH$_2$—, —(CH$_2$)$_{10}$—, and the like. Included within this definition are the terms "$C_1$–$C_4$ alkylidene" and "$C_2$–$C_4$ alkylidene".

The term "$C_4$–$C_8$ cycloalkyl" refers to a cycloalkyl ring of four to eight carbon atoms, such as cyclobutyl, cyclopentyl, cyclohexyl, 4,4-dimethylcyclohexyl, cycloheptyl, cyclooctyl, and the like.

The term "straight or branched chain divalent hydrocarbyl residue of one to eight carbon atoms" refers to a divalent radical derived from a straight or branched alkane, alkene, or alkyne of one to eight carbon atoms. Depending upon the branching and number of carbon atoms, as will be appreciated by organic chemists, such a moiety can contain one, two or three double or triple bonds, or combinations of both. As such, this term can be considered an alkylidene group as defined above containing from 1 to 8 carbon atoms optionally containing one to three double or triple bonds, or combinations of the two, limited as noted in the preceding sentence.

This invention includes the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

This invention includes both mono-salt forms, i.e., a 1:1 ratio of a compound of Formula I with a base as previously described, as well as di-salt forms in those instances where a compound of Formula I has two acidic groups. In addition, this invention includes any solvate forms of the compounds of Formula I or salts thereof, such as ethanol solvates, hydrates, and the like.

It is recognized that in compounds having branched alkyl, alkylidenyl, or hydrocarbyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, ie, (1H)-5-tetrazolyl and (2H)-5-tetrazolyl.

PREFERRED EMBODIMENTS

A most preferred group of compounds employed in the methods of the present invention are those compounds of Formula Ia:

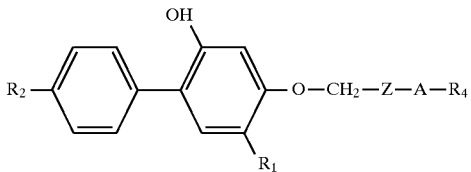

and pharmaceutically acceptable base addition salts thereof. Especially preferred are those compounds wherein $R_2$ is halo, particularly fluoro. Preferred $R_1$ substituents are propyl and especially ethyl.

Preferred Z substituents include $C_2$–$C_4$ alkylidene, particularly —$CH_2CH_2$— and —$CH_2CH_2CH_2CH_2$—. Preferred A groups include —O—, —$CH_2$—, —$CH(R_7$-substituted phenyl)-, and —$C(CH_3)_2$—.

Preferred $R_4$ groups include —COOH, 5-tetrazolyl, or a mono-, di-, or tri-cyclic group as drawn above wherein there is at least one acidic group attached to a ring, such as —W—COOH, —T—G—COOH, or the corresponding tetrazole derivatives. The preferred W moiety is that of a bond or straight chain $C_1$–$C_4$ alkylidene; preferred G moieties are straight chain $C_1$–$C_4$ alkylidene. It is preferred that $R_5$ or $R_7$ be $C_1$–$C_4$ alkyl, especially n-propyl.

Particularly preferred groups are those wherein A is —CH($R_7$-substituted phenyl)- and $R_4$ is —COOH or 5-tetrazolyl. Also preferred are those compounds wherein A is —O— and $R_4$ is

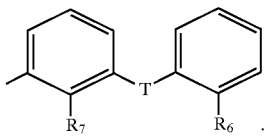

Preferred aspects of this substructure are those therein $R_7$ is $C_1$–$C_4$ alkyl, especially n-propyl, and $R_6$ is —W—COOH. Particularly preferred are those compounds wherein T is —O— or —S— and W is a bond.

Particuarly preferred compounds of the instant invention include 2-[2-propyl-3-[3-[2-ethyl-4-(4-fluorophenyl)-5-hydroxyphenoxy]propoxy]phenoxy]benzoic acid; 3-(2-(3-(2-ethyl-4-(4-fluorophenyl)-5-hydroxyphenoxy)propoxy)-6-(4-carboxy-phenoxy)phenyl)propionic acid; 1-(4-(carboxy-methoxy)phenyl)-1-(1H-tetrazol-5-yl)-6-(2-ethyl-4-(4-fluorophenyl)-5-hydroxyphenoxy)hexane; 3-[4-[7-carboxy-9-oxo-3-[3-[2-ethyl-4-(4-fluorophenyl)-5-hydroxyphenoxy]-propoxy]-9H-xanthene]]propanoic acid; and 5-[3-[2-(1-carboxy)-ethyl]-4-[3-[2-ethyl-4-(4-fluorophenyl)-5-hydroxyphenoxy]-propoxy]phenyl]-4-pentynoic acid; or a pharmaceutically acceptable salt or solvate thereof.

The leukotriene $B_4$ ($LTB_4$) antagonists employed in the methods of the present invention may be synthesized essentially as described in U.S. Pat. No. 5,462,954 issued Oct. 31, 1995, the entire contents of which are herein incorporated by reference.

The following examples further illustrate the preparation of the compounds employed in this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million (__) relative to tetramethylsilane. Chemical shifts of aromatic protons of quinoline species in DMSO-$d_6$ are concentration dependent. The following abbreviations are used to denote signal patterns: s=singlet, d=doublet, t=triplet, q=quartet, b=broad, m=multiplet. Infrared spectra were determined on a Nicolet DX10 FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1

3-[2-[3-[(5-Ethyl-2-hydroxy[1,1'-biphenyl]-4-yl)oxy]propoxy]-1-dibenzofuran]propanoic acid disodium salt

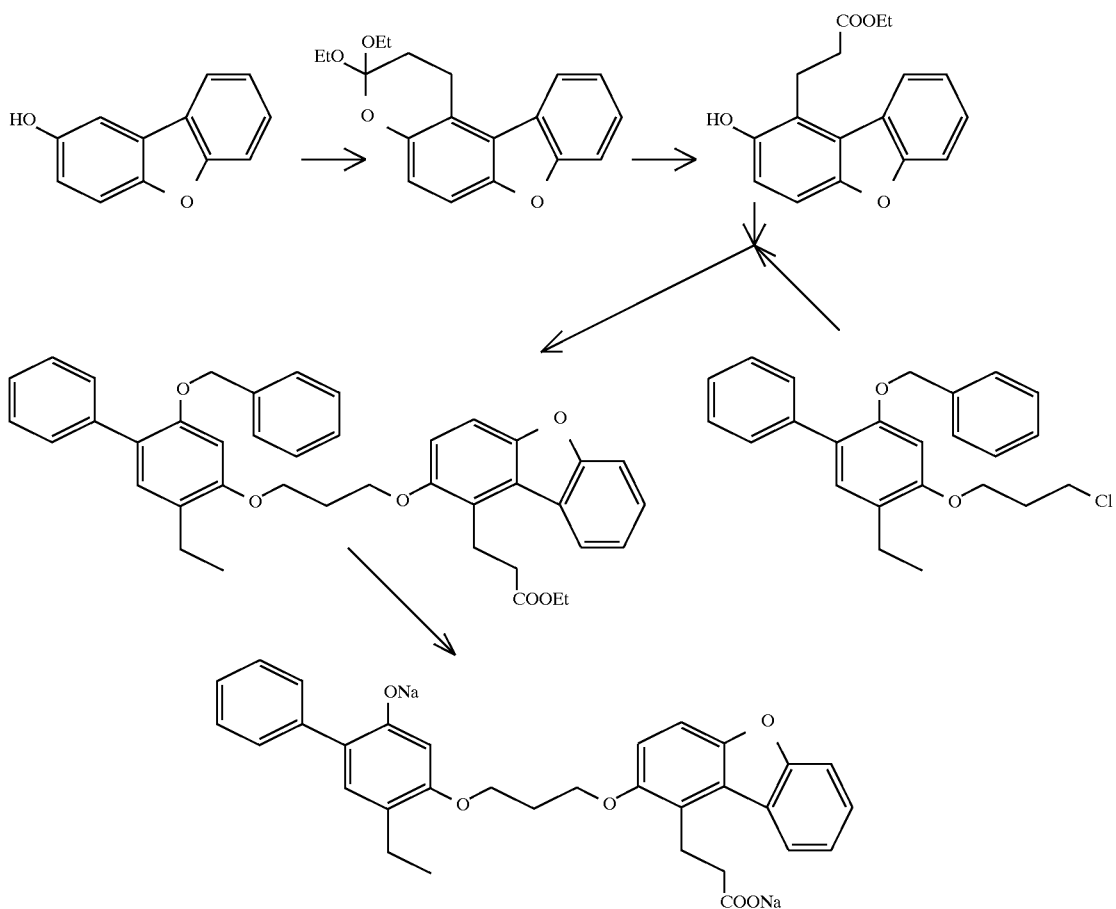

A. Preparation of 3,3-diethoxy-2,3-dihydro-1H-benzofuro-[3,2-f][1]benzopyran.

A solution of 2-hydroxydibenzofuran (5.00 g, 27.2 mmol), triethylorthoacrylate (10.1 g, 54.3 mmol) and pivalic acid (1.39 g, 13.6 mmol) in toluene (100 mL) was refluxed for 18 hours. The mixture was cooled to room temperature and washed once with water and once with a saturated sodium bicarbonate solution, dried over sodium sulfate, filtered and concentrated in vacuo to provide an orange oil. This material was diluted with hexane and maintained at −20° C. for 18 hours. The resulting crystals were collected via vacuum filtration to provide 5.67 g (67%) of the desired title intermediate, mp 64° C.; NMR (CDCl$_3$) 7.96 (d, J=7.8 Hz, 1H), 7.57 (d, J=8.0 Hz, 1H), 7.46 (t, J=8 Hz, 1H), 7.35 (m, 2H), 7.06 (d, J=8.8 Hz, 1H), 3.82 (q, J=7.2 Hz, 2H), 3.73 (q, J=6.8 Hz, 2H), 3.35 (t, J=6.9 Hz, 2H), 2.29 (t, J=7.0 Hz, 2H), 1.23 (t, J=7.1 Hz, 6H); MS-FD m/e 312 (p); IR (CHCl$_3$, cm$^{-1}$) 2982, 1494, 1476, 1451, 1434, 1251, 1090, 1054, 975.

Analysis for $C_{19}H_{20}O_4$: Calc: C, 73.06; H, 6.45; Found: C, 72.81; H, 6.72.

B. Preparation of 3-[1-(2-hydroxydibenzofuran)]-propanoic acid ethyl ester.

A mixture of 3,3-diethoxy-2,3-dihydro-1H-benzofuro-[3,2-f][1]benzopyran (3.50 g, 11.2 mmol) and 10% aqueous hydrochloric acid (5 mL) in ethyl acetate (30 mL) was stirred at room temperature for 1 hour. The resulting mixture was washed once with water, dried over sodium sulfate, filtered and concentrated in vacuo to provide a tan solid. Recrystallization from hexane/ethyl acetate provided 3.11 g (98%) of the desired title intermediate as an off-white crystalline material: mp 128°–131° C.; NMR (CDCl$_3$) 7.88 (d, J=7.7 Hz, 1H), 7.59 (d, J=8.4 Hz, 1H), 7.47 (t, J=7.2 Hz, 1H), 7.37 (d, J=8.9 Hz, 1H), 7.36 (t, J=6.6 Hz, 1H), 7.13 (d, J=8.8 Hz, 1H), 7.13 (q, J=8.8 Hz, 2H), 3.43 (t, J=5.8 Hz, 2H), 3.01 (t, J=7.7 Hz, 2H), 1.23 (t, J=7.2 Hz, 3H); MS-FD m/e 284 (100, p), 256 (65), 238 (17); IR (KBr, cm$^{-1}$) 2985 (b), 1701, 1430, 1226, 1183, 1080.

Analysis for $C_{17}H_{16}O_4$: Calc: C, 71.82; H, 5.67; Found: C, 71.90; H, 5.43.

C. Preparation of 3-[2-[3-[[5-ethyl-2-(phenylmethoxy)-[1,1'-biphenyl]-4-yl]oxy]propoxy]-1-dibenzofuran] propanoic acid ethyl ester.

3-[1-(2-Hydroxydibenzofuran)]propanoic acid ethyl ester (625 mg, 2.20 mmol) was dissolved in dimethylformamide (10 mL) and carefully treated at room temperature with 95% sodium hydride (58 mg, 2.4 mmol). When gas evolution had ceased, 2-benzyloxy-1-phenyl-5-ethyl-4-(3-chloro-1-propyloxy)benzene (836 mg, 2.20 mmol) was added and the resulting mixture was stirred for 18 hours. The mixture was diluted with ether and washed once with water. The organic layer was dried over sodium sulfate, filtered, and concentrated in vacuo to provide a dark oil. Silica gel chromatography (ethyl acetate/hexane) provided 200 mg (14%) of the desired titled intermediate as a colorless oil: NMR (CDCl$_3$) 8.11 (d, J=7.7 Hz, 1H), 7.57 (m, 3H), 7.48 (t, J=7.3 Hz, 1H), 7.20–7.44 (m, 10 H), 7.17 (s, 1H), 7.08 (d, J=8.9 Hz, 1H), 6.67 (s, 1H), 5.05 (s, 2H), 4.29 (t, J=6.2 Hz, 2H), 4.26 (t, J=6.1 Hz, 2H), 4.15 (q, J=7.2 Hz, 2H), 3.54 (t, J=8.5 Hz, 2H), 2.67 (m, 4H), 2.37 (t, J=6.0 Hz, 2H), 1.21 (m, 6H)

D. Preparation of 3-[2-[3-[(5-ethyl-2-hydroxy[1,1'-biphenyl]-4-yl)oxy]propoxy]-1-dibenzofuran]propanoic acid disodium salt.

To a nitrogen-purged solution of 3-[2-[3-[[5-ethyl-2-(phenylmethoxy) [1,1'-biphenyl]-4-yl]oxy]propoxy]-1-dibenzofuran]propanoic acid ethyl ester (200 mg, 0.318 mmol) in a 1:1 mixture of methanol/tetrahydrofuran (40 mL) was added 10% palladium on carbon (25 mg). The resulting suspension was hydrogenated at 1 atm pressure for 24 hours at room temperature. The mixture was filtered through a short pad of Florisil® and the filtrate concentrated in vacuo. The residue was dissolved in a 1:1 mixture of methanol/tetrahydrofuran (20 mL) and treated with 5N sodium hydroxide solution (2 mL) at room temperature for 24 hours. The resulting mixture was extracted once with diethyl ether. The aqueous layer was acidified with 5N hydrochloric acid solution and extracted twice with methylene chloride. The combined methylene chloride fractions were concentrated in vacuo. The residue was dissolved in a minimum of 1N sodium hydroxide solution and purified on HP-20 resin to provide 53 mg (30%) of the desired title product as a fluffy white solid: NMR (DMSO-$d_6$) 8.12 (d, J=6.9 Hz, 1H), 7.64 (d, J=8.2 Hz, 1H), 7.37–7.57 (m, 5H), 7.30 (m, 2H), 7.14 (m, 2H), 6.96 (S, 1H), 6.93 (S, 1H), 4.30 (t, J=7.3 Hz, 2H), 4.14 (t, J=5.4 Hz, 2H), 2.48 (m, 4H), 2.23 (m, 4H), 1.10 (t, J=7.6 Hz, 3H); MS-FAB m/e 555 (88, p+1), 533 (62); IR (CHCl$_3$, cm$^{-1}$) 3384 (b), 2969, 1566, 1428, 1257, 1181.

Analysis for $C_{32}H_{28}O_6Na_2$: Calc: C, 69.31; H, 5.09; Found: C, 69.51; H, 5.39.

EXAMPLE 2

7-Carboxy-9-oxo-3-[3-(2-ethyl-5-hydroxy-4-phenylphenoxy)propoxy]-9H-xanthene-4-propanoic acid disodium salt monohydrate propanoate (729 mg, 1.97 mmol), potassium carbonate (1.36 g, 9.85 mmol) and potassium iodide (33 mg, 0.20 mmol) was refluxed for 24 hours. Dimethylsulfoxide (2 mL) was added and heating continued for 24 hours. The reaction mixture was cooled to room temperature, diluted with ethyl acetate, and washed once with water. The organic layer was dried over sodium sulfate, filtered and concentrated in vacuo to reveal a tan solid. This material was dissolved in ethyl acetate (30 mL) and the resulting solution purged with nitrogen. To this solution was added 10% palladium on carbon (120 mg) and the resulting suspension hydrogenated at 1 atmosphere of pressure. The solution was filtered and concentrated in vacuo to provide a colorless oil. This material was dissolved in a solution of 1:1 methanol/tetrahydrofuran (30 mL) and treated with 5N sodium hydroxide solution (2 mL) at room temperature for 18 hours. The resulting solution was extracted once with diethyl ether and the aqueous layer acidified with 5N hydrochloric acid solution. The resulting precipitate was collected via suction filtration. This material was converted to the di-sodium salt and purified as described above for the preparation of Example 1(D) to provide 390 mg (56%) of the desired title product as a fluffy white solid: NMR (DMSO-$d_6$) 12.65 (s, 1H, —OH), 8.65 (s, 1H), 8.28 (dd, J 8.5, 2.0 Hz, 1H), 8.01 (d, J=8.9 Hz, 1H), 7.50 (m, 3H), 7.29 (t, J 7.8 Hz, 2H), 7.17 (m, 2H), 6.93 (s, 1H), 6.89 (s, 1H), 4.26 (m, 4H), 3.12 (m, 2H), 2.47 (m, 2H), 2.23 (m, 2H), 1.10 (t, J=7.4 Hz, 3H); MS-FAB m/e 627 (24, p), 605 (40), 583 (24), 331 (24), 309 (100); IR (KBr, cm$^{-1}$) 3419 (b), 2962, 1612, 1558, 1443, 1390, 1277, 1084.

Analysis for $C_{34}H_{28}O_9Na_2 \cdot H_2O$: Calc: C, 63.34; H, 4.69; Found: C, 63.36; H, 4.50.

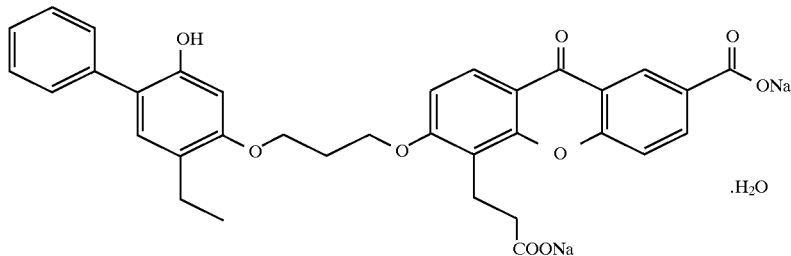

A mixture of 2-benzyloxy-1-phenyl-5-ethyl-4-(3-chloro-1-propyloxy)benzene (749 mg, 1.97 mmol), ethyl 7-carboethoxy-3-hydroxy-9-oxo-9H-xanthene-4-

EXAMPLE 3

2-[2-Propyl-3-[3-[2-ethyl-4-(4-fluorophenyl)-5-hydroxyphenoxy]propoxy]phenoxy]benzoic acid sodium salt

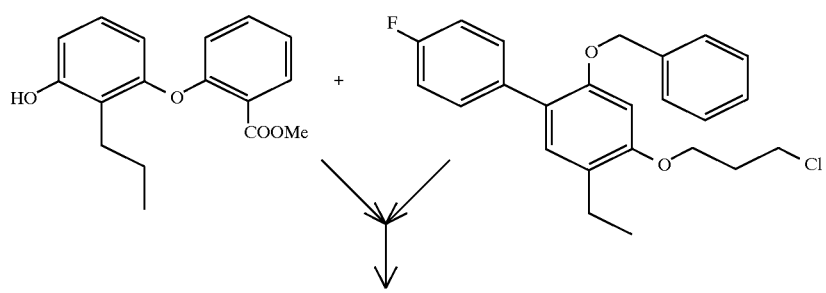

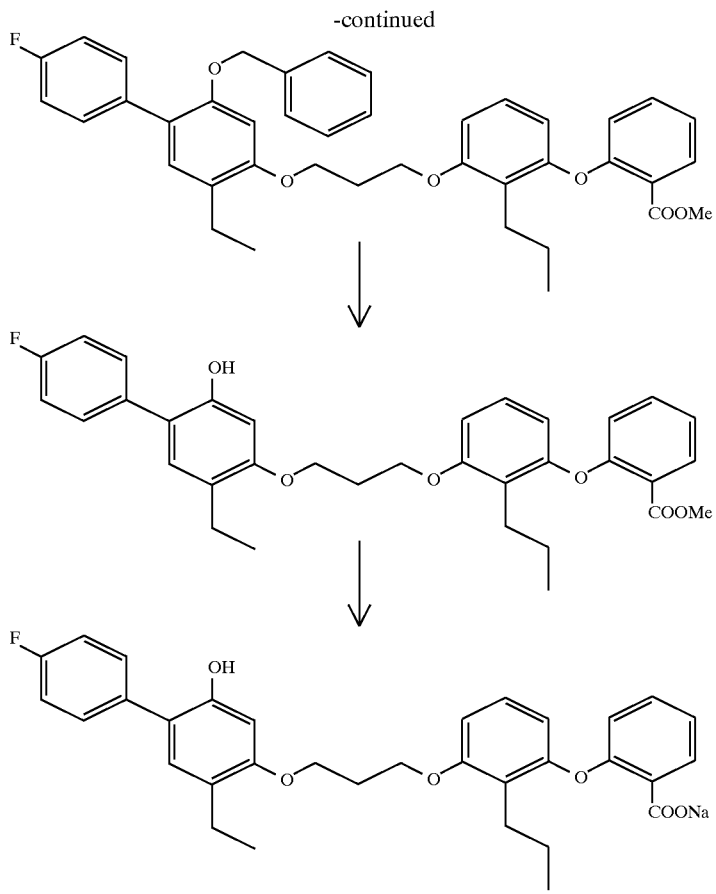

A. Preparation of 2-[2-propyl-3-[3-[2-ethyl-4-(4-fluorophenyl)-5-(phenylmethoxy)phenoxy]propoxy]phenoxy]-benzoic acid methyl ester.

A mixture of 2-benzyloxy-1-(4-fluorophenyl)-5-ethyl-4-(3-chloro-1-propyloxy)benzene (20.0 g, 50.2 mmol) and sodium iodide (75.3 g, 502 mmol) in 2-butanone (200 mL) was refluxed for 6 hours. The mixture was diluted with ether and washed once with water. The organic layer was dried over sodium sulfate, filtered, and concentrated in vacuo to provide a colorless oil. This material was dissolved in dimethylformamide (100 mL) and treated with 2-(3-hydroxy-2-propylphenoxy)benzoic acid methyl ester (14.4 g, 50.2 mmol) and potassium carbonate (20.8 g, 151 mmol) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (d, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p); IR (CHCl$_3$, cm$^{-1}$) 2960, 1740, 1604, 1497, 1461, 1112.

Analysis for C$_{41}$H$_{41}$O$_6$F: Calc: C, 75.91; H, 6.37; Found: C, 76.15; H, 6.45.

B. Preparation of 2-[2-propyl-3-[3-[2-ethyl-4-(4-fluorophenyl)-5-hydroxyphenoxy]propoxy]phenoxy] benzoic acid methyl ester.

2-[2-Propyl-3-[3-[2-ethyl-4-(4-fluorophenyl)-5-(phenylmethoxy)phenoxy]propoxy]phenoxy]benzoic acid methyl ester (33.0 g, 50.9 mmol) was de-benzylated as described above for the preparation of Example 2 to provide 27.3 g (96%) of the title intermediate as an amber oil: NMR (CDCl$_3$) 7.90 (dd, J=7.8, 1.7 Hz, 1H), 7.42 (m, 3H), 7.05–7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, -OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p); IR (CHCl$_3$, cm$^{-1}$) 2965, 1727, 1603, 1496, 1458, 1306, 1112.

Analysis for C$_{34}$H$_{35}$O$_6$F: Calc: C, 73.10; H, 6.31; Found: C, 73.17; H, 6.42.

C. Preparation of 2-[2-propyl-3-[3-[2-ethyl-4-(4-fluorophenyl)-5-hydroxyphenoxy]propoxy]phenoxy] benzoic acid sodium salt.

2-[2-Propyl-3-[3-[2-ethyl-4-(4-fluorophenyl)-5-hydroxyphenoxy]propoxy]phenoxy]benzoic acid methyl ester (21.5 g, 38.5 mmol) was hydrolyzed as described above for the preparation of Example 2. The acid was converted to the sodium salt and purified as described above for the preparation of Example 1(D) to provide 16.7 g (77%) of the desired title product as a white amorphous solid: NMR (DMSO-d$_6$) 10.50 (bs, 1H, -OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9 Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112.

Analysis for $C_{33}H_{32}O_6FNa$: Calc: C, 69.95; H, 5.69; F, 3.35; Found: C, 69.97; H, 5.99; F, 3.52.

As discussed above, an ischemic stroke may result from either embolic or thrombotic occlusion of an intracerebral artery, a distinction that is often difficult to make on clinical grounds. Nearly 50 percent of patients with stroke have had one or more preminitory TIAS.

The diagnosis of cerebral focal stoke is strongly supported by the presence of conditions that predispose to embolus formation, such as mitral stenosis, atrial fibrillation, endocarditis, or myxomatous mitral valve prolapse. In addition to dislodged thrombi, emboli may also consist of fat, tumor cells, and air or nitrogen bubbles.

Stroke symptoms generally evolve rapidly, often becoming maximal within seconds to minutes. Occasionally, stroke progresses over minutes or hours, and, rarely, stepwise over days or weeks.

Factors leading to the development of cerebral focal stroke fall mainly into two categories:

1. Disorder of cranial blood vessels. By far, the most common cause of cerebral thrombosis is atherosclerosis, very often associated with hypertension, diabetes mellitus, and coronary artery or peripheral vascular disease. Inflammatory blood vessel disorders, which occur in syphilis, tuberculosis, temporal arteritis, or collagen vascular disease or as a result of radiation injury, may also predispose to thrombus formation. Trauma to the head and neck may cause dissection or thrombosis of major arteries.

2. Disorders of the cardiovascular system. Stroke may follow systemic hypotension from myocardial infarction, heart block, shock, surgical anesthesia, or overly vigorous treatment of chronic hypertension.

Stroke usually can be diagnosed clinically, especially in a person over age 50 with hypertension, diabetes mellitus, or signs of atherosclerosis, or in anyone with a known source of emboli. In the unusual case, differentiation from a rapidly growing or suddenly symptomatic tumor is aided by a CT or MRI scan (which is sometimes negative for as long as several days after an acute infarction). Arteriography is limited to patients in whom the diagnosis is in doubt or remedial vascular obstruction is suspected.

A stroke due to a large embolus tends to be an acute completed stroke, sudden in onset, with focal disorders that are maximal within minutes. Headache may precede it. Thrombosis, which is less frequent, is suggested by a slower onset or gradually progressing symptoms (as in evolving stroke). However, the distinction is not entirely reliable. Concomitant signs of MI, atrial fibrillation, or vegetative heart disease further suggest embolization.

Other than aspirin, ticlopidine is the only antiplatelet agent that has been clearly shown to be effective for stroke prevention. Endarterectomy may be indicated in patients with 70 to 99 percent narrowing of a symptomatic internal carotid artery. However, most authorities agree that carotid endarterectomy is not indicated in patients with TIAs that are referable to the basilar-vertebral system, in patients with significant deficits from prior strokes, or in patients in whom a stroke is evolving.

Heparin may stabilize symptoms in evolving stroke, but anticoagulants are useless (and possibly dangerous) in acute completed stroke, and are contraindicated in hypertensives because of the increased possibility of hemorrhage into the brain or other organs. Although the timing is controversial, anticoagulants may be started to prevent recurrent cardiogenic emboli. Clot lysing agents, including tissue plasminogen activator and streptokinase, are being evaluated for the very early treatment of acute stroke. Nimodipine has recently been shown to improve survival and clinical outcome after ischemic stroke.

To be effective, treatments to minimize brain damage from acute stroke have to begin very soon after stroke onset.

The methods of the present invention describe the use of leukotriene antagonists for the prevention and treatment of cerebral focal stroke, which is characterized by the excessive release of leukotriene $B_4$.

The term "excessive release" of a leukotriene refers to an amount of the leukotriene sufficient to cause cerebral focal stroke. The amount of leukotriene which is considered to be excessive will depend on a variety of factors, including the amount of leukotriene required to cause the disease, and the species of the mammal involved. As will be appreciated by those skilled in the art, the success of treating a mammal suffering from cerebral focal stroke by an excessive release of leukotriene with a compound of Formula I will be measured by the regression or prevention of the symptoms of the condition.

Assays

Assay 1

The effectiveness of compounds of Formula I to inhibit the binding of tritiated $LTB_4$ to guinea pig lung membranes was determined as follows.

[$^3$H]-$LTB_4$ Radioligand Binding Assay in Guinea Pia Luna Membranes

[$^3$H]-$LTB_4$ (196–200 Ci/mmole) was purchased from New England Nuclear (Boston, Mass.). All other materials were purchased from Sigma (St. Louis, Mo.). Incubations (555 mL) were performed in polypropylene minitubes for 45 minutes at 30° C. and contained 25 mg of guinea pig lung membrane protein (Silbaugh, et al., *European Journal of Pharmacolocy*, 223 (1992) 57–64) in a buffer containing 25 mM MOPS, 10 mM $MgCl_2$, 10 mM $CaCl_2$, pH 6.5, approximately 140 pM [$^3$H]-$LTB_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 mM $LTB_4$ and was usually less than 10% of total binding. Data were analyzed using linear regression analysis of log-logit plots of the values between 10% and 90% of control binding to calculate $IC_{50}$s and slope factors (pseudo-Hill coefficients). $IC_{50}$ values thus obtained were corrected for radioligand concentration (Cheng and Prusoff, *Biochem. Pharmacol.*, 22, 3099 (1973)) to calculate Ki values. pKi is the mean -log Ki for n experiments.

Compounds of the instant invention tested in the above assay were found to have a pKi of between 7 and 11.

The ability of a compound of formula I to limit effectively neuronal tissue damage can be evaluated in a variety of experimental stroke models (Hunter, et al., TiPS 16, 123–8, 1995). The methodology for testing the compound's effect in ameliorating ischemic cell damage after transient middle cerebral artery occlusion (Zhang, et al., Stroke 26, 1438–43, 1995) is given as one example.

Assay 2

Male rats weighing approximately 300 grams are anesthetized with 3.5% halothane and maintained with 1.0% halothane in 70% $N_2O$ and 30% $O_2$ with the use of a face mask. Rectal temperature is maintained at 37° C. throughout the surgical procedure. The right femoral artery and vein are cannulated for measuring blood gases before inducing ischemia, monitoring blood pressure during the surgery and administering compound.

Approximately 18 mm of 4-0 surgical nylon suture with a rounded tip is advanced from the external carotid artery into the lumen of the internal carotid artery until it blocks the origin of the middle cerebral artery (MCA). Two hours after MCA occlusion animals are reanesthetized and reperfusion allowed to occur by withdrawing the filament until the tip becomes visible at the origin of the lumen of the external carotid artery. Compound is given by infusing it intravenously over a 3-minute interval at 1, 11, and 22 hours after reperfusion is initiated. Animals are killed 48 hours after reperfusion by giving them ketamine (44 mg/kg) IM and xylazine (13 mg/kg IM). Each rat is transcardially perfused with heparinized saline and 10% formalin before removing the brain. The brain tissue is processed, embedded in paraffin and 6-$\mu$m-thick sections cut from each block and stained with hematoxylin and eosin. Infarct volume is measured blindly with the use of a Global Lab Image analysis program (Data Translation). The infarct area and the ipsilateral and contralateral hemispheric area are calculated in square millimeters by tracing the right and left hemispheres and the ischemic lesion on the computer screen. The volumes in cubic millimeters are determined by multiplying the area by the section interval thickness. Infarct volume is analyzed as a percentage of the whole hemisphere. To determine dose-response effects, animals are divided into 5 experimental groups of 10 rats each. The groups are: sham-treated rats given vehicle, stroke-impaired rats given either vehicle or doses of either 0.5, 1.0, or 2.0 mg/kg of a compound of formula I in saline. The effectiveness of a treatment is accessed by comparing the size of the infarct of the treated group to that of the vehicle control.

The therapeutic and prophylactic treatments provided by this invention are practiced by administering to a mammal in need thereof a dose of a compound of formula I or a pharmaceutically acceptable salt or solvate thereof, that is effective to inhibit or treat cerebral focal stroke.

The term "inhibit" includes its generally accepted meaning which includes prohibiting, preventing, restraining and slowing, stopping or reversing progression, severity or a resultant symptom. As such, the present method includes both medical therapeutic and/or prophylactic administration as appropriate.

While it is possible to administer a compound employed in the methods of this invention directly without any formulation, the compounds are usually administered in the form of pharmaceutical formulation comprising a pharmaceutically acceptable excipient and at least one compound of the present invention. The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See, e.g., REMINGTON'S PHARMACEUTICAL SCIENCES, ( 16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets, and injectable solutions. Especially preferred are capsules and tablets.

The therapeutic and prophylactic treatments provided by this invention are practiced by administering to a mammal in need thereof a dose of a compound of formula I or a pharmaceutically acceptable salt or solvate thereof that is effective to inhibit or treat cerebral focal stroke.

Advantageously for this purpose, formulations may be provided in unit dosage form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

While all of the compounds illustrated above exemplify $LTB_4$ inhibition activity in vitro, we have also discovered that compounds bearing a single acidic group ($R_6$) are considerably more orally bioactive when administered to mammals compared with those compounds bearing two such acidic groups. Thus, a preferred embodiment when administering compounds of Formula I orally to mammals comprises administering compounds bearing a single acidic $R_6$ functionality.

The following formulation examples may employ as active compounds any of the compounds of this invention. The examples are illustrative only and are not intended to limit the scope of the invention in any way.

Formulation 1
Hard gelatin capsules are prepared using the following ingredients:

| | Quantity (mg/capsule) |
|---|---|
| 3-(2-(3-(2-Ethyl-4-(4-fluorophenyl)-5-hydroxyphenoxy)propoxy)-6-(4-carboxy-phenoxy)phenyl)propanoic acid | 250 |
| Starch | 200 |
| Magnesium stearate | 10 |

The above ingredients are mixed and filled into hard gelatin capsules in 460 mg quantities.

Formulation 2
A tablet is prepared using the ingredients below:

| | Quantity (mg/tablet) |
|---|---|
| 1-(4-(Carboxymethoxy)phenyl)-1-(1H-tetrazol-5-yl)-6-(2-ethyl-4-(4-fluorophenyl)-5-hydroxyphenoxy)hexane | 250 |
| Cellulose, microcrystalline | 400 |
| Silicon dioxide, fumed | 10 |
| Magnesium stearate | 5 |

The components are blended and compressed to form tablets each weighing 665 mg.

Formulation 3
An aerosol solution is prepared containing the following components:

| | Weight % |
|---|---|
| 3-[4-[7-Carboxy-9-oxo-3-[3-[2-ethyl-4-(4-fluorophenyl)-5-hydroxyphenoxy]propoxy]-9H-xanthene]]propanoic acid | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

Formulation 4
Tablets each containing 60 mg of active ingredient are made up as follows:

| | |
|---|---|
| 2-[2-Propyl-3-[3-[2-ethyl-5-hydroxy-4-(4-fluorophenyl)phenoxy]propoxy]phenoxy]-benzoic acid sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules each containing 80 mg of medicament are made as follows:

| | |
|---|---|
| 5-[3-[2-(1-Carboxy)ethyl]-4-[3-[2-ethyl-4-(4-fluorophenyl)-5-hydroxyphenoxy]propoxy]-phenyl]-4-pentynoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6
Suppositories each containing 225 mg of active ingredient are made as follows:

| | |
|---|---|
| 3-(2-(3-(2-Ethyl-4-(4-fluorophenyl)-5-hydroxyphenoxy)propoxy)-6-(4-carboxy-phenoxy)phenyl)propanoic acid | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

Formulation 7
Suspensions each containing 50 mg of medicament per 5 mL dose are made as follows:

| | |
|---|---|
| 2-[2-Propyl-3-[3-[2-ethyl-4-(4-fluorophenyl)-5-hydroxyphenoxy]propoxy]phenoxy]benzoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 mL |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

Formulation 8
An intravenous formulation may be prepared as follows:

| | |
|---|---|
| 2-[2-propyl-3-[3-[2-ethyl-4-(4-fluorophenyl)-5-hydroxyphenoxy]propoxy]phenoxy]benzoic acid | 100 mg |
| Isotonic saline | 1,000 ml |

The solution of the above ingredients generally is administered intravenously to a subject at a rate of 1 ml per minute.

We claim:

1. A method for preventing or treating cerebral focal ischemia in a mammal which comprises administering to a mammal in need thereof an effective amount of a compound of the formula I

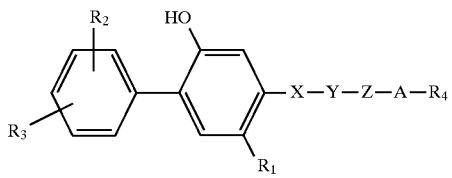

wherein:

$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substituted phenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)-S(O)q-, trifluoromethyl, or di-($C_1$–$C_3$ alkyl)amino;

X is —O—, —S—, —C(=O), or —CH$_2$—;

Y is —O— or —CH$_2$—;

or when taken together, —X—Y— is —CH=CH— or —C≡C—;

Z is a straight or branched chain $C_1$–$C_{10}$ alkylidenyl;

A is a bond, —O—, —S—, —CH=CH—, or CRaRb—, where $R_a$ and $R_b$ are each independently hydrogen, $C_1$–$C_5$ alkyl, or R7-substituted phenyl, or when taken together with the carbon atom to which they are attached form a $C_4$–$C_8$ cycloalkyl ring;

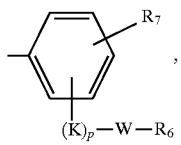

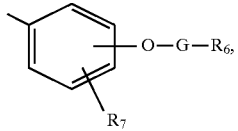

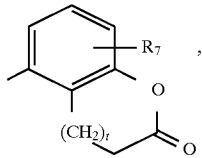

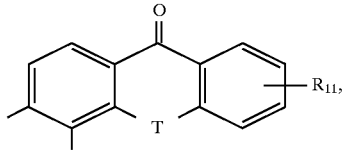

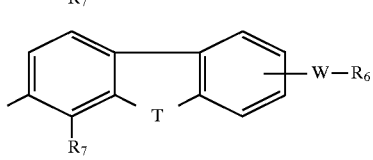

or

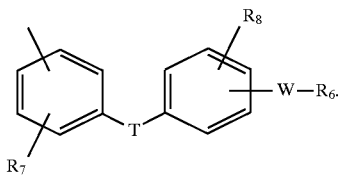

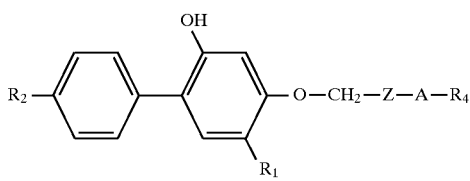

where, each $R_6$ is independently —COOH, 5-tetrazolyl, —CON($R_9$)$_2$, or —CONHSO$_2$R$_{10}$;

each $R_7$ is hydrogen, $C_1$–$C_4$ alkyl, $C_2$–$C_5$ alkenyl, $C_2$–$C_5$ alkynyl, benzyl, methoxy, -W-$R_6$, -T-G-$R_6$, ($C_1$–$C_4$ alkyl)-T-($C_1$–$C_4$ alkylidenyl)—O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, -W-$R_6$, or -T-G-$R_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)q—;

K is —C(=O)— or —CH(OH)—;

each q is independently 0, 1, or 2;

p is 0 or 1; and t is 0 or 1;

provided when X is —O— or —S—, Y is not —O—;

provided when A is —— or —S—, $R_4$ is not $R_6$;

provided when A is —O— or —S— and Z is a bond, Y is not —O—; and provided W is not a bond when p is 0;

or a pharmaceutically acceptable salt or solvate thereof.

2. The method as claimed in claim 1 employing a compound of the formula or a pharmaceutically acceptable salt or solvate thereof.

3. The method as claimed in claim 2 employing 2-[2-propyl-3- [3- [2-ethyl-4- (4-fluorophenyl)-5-hydroxphenoxy]propoxy]phenoxy]benzoic acid or a pharmaceutically acceptable salt or solvate thereof.

4. The method as claimed in claim 2 employing 3-(2-(3-(2-ethyl-4-(4-fluorophenyl)-5-hydroxyphenoxy) propoxy)-6- (4-carboxy-phenoxy)phenyl)propionic acid or a pharmaceutically acceptable salt or solvate thereof.

5. The method as claimed in claim 2 employing 1-(4-(carboxy-methoxy)phenyl)-1-(1H-tetrazol-5-yl)-6-(2-ethyl-4- (4-f luorophenyl)-5-hydroxyphenoxy)hexane or a pharmaceutically acceptable salt or solvate thereof.

6. The method as claimed in claim 2 employing 3-[4-[7-carboxy-9-oxo-3- [3- [2-ethyl-4- (4-fluorophenyl)-5-hydroxyphenoxy]-propoxy]-9H-xanthene]]propanoic acid or a pharmaceutically acceptable salt or solvate thereof.

7. The method as claimed in claim 2 employing 5-[3-[2-(1-carboxy)-ethyl]-4-[3-[2-ethyl-4-(4-fluorophenyl)-5-hydroxyphenoxy]-propoxy]phenyl]-4-pentynoic acid or a pharmaceutically acceptable salt or solvate thereof.

8. The method as claimed in any one of claim 1 in which the mammal is a human.

9. The method as claimed in any one of claim 2 in which the mammal is a human.

10. The method as claimed in any one of claim 3 in which the mammal is a human.

11. The method as claimed in any one of claim 4 in which the mammal is a human.

12. The method as claimed in any one of claim 5 in which the mammal is a human.

13. The method as claimed in any one of claim 6 in which the mammal is a human.

14. The method as claimed in any one of claim 7 in which the mammal is a human.

* * * * *